(12) United States Patent
Kretschmar et al.

(10) Patent No.: US 7,863,420 B2
(45) Date of Patent: *Jan. 4, 2011

(54) PROCESS FOR REMOVING FIBRONECTIN FROM PLASMA FRACTIONS

(75) Inventors: Michael Kretschmar, Seligenstadt (DE); Wolfgang Moeller, Oberusel (DE)

(73) Assignee: Biotest AG, Dreieich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/594,453

(22) PCT Filed: Sep. 9, 2005

(86) PCT No.: PCT/EP2005/009730

§ 371 (c)(1),
(2), (4) Date: Sep. 26, 2006

(87) PCT Pub. No.: WO2006/029775

PCT Pub. Date: Mar. 23, 2006

(65) Prior Publication Data

US 2007/0203330 A1    Aug. 30, 2007

(30) Foreign Application Priority Data

Sep. 14, 2004 (DE) .......... 10 2004 044 429

(51) Int. Cl.
C07K 14/00 (2006.01)
C07K 14/745 (2006.01)
C07K 1/14 (2006.01)
C07K 1/22 (2006.01)

(52) U.S. Cl. .............. 530/380; 530/350; 530/412; 530/415; 530/418

(58) Field of Classification Search .......... 424/101; 530/383
See application file for complete search history.

(56) References Cited

U.S. PATENT DOCUMENTS

| | | | |
|---|---|---|---|
| 4,341,764 A * | 7/1982 | Wallace et al. .................. 514/2 |
| 4,774,323 A | 9/1988 | Newman et al. |
| 4,789,733 A * | 12/1988 | Winkelman .................. 530/383 |
| 5,128,245 A | 7/1992 | Greenberg et al. |
| 5,408,039 A * | 4/1995 | Burnouf-Radosevich et al. . 530/383 |
| 5,441,635 A | 8/1995 | Ichitsuka et al. |
| 5,710,254 A * | 1/1998 | Newman et al. ............. 530/383 |
| 6,465,624 B1 | 10/2002 | Fischer et al. |
| 2007/0135619 A1 | 6/2007 | Kretschmar et al. |
| 2007/0299250 A1 | 12/2007 | Kretschmar et al. |

OTHER PUBLICATIONS

Zykova T A et al., "A Simple and Effective Additional Step in Purification of Bovine Blood Serum Fibronectin", XP002352960, BIOSIS Database Accession No. PREV19847804777 (1983).
Written Opinion of the International Searching Authority issued in PCT/EP05/009730 (PCT/ISA/237).
Federici, Augusto B., "The Factor VIII/von Willebrand Factor Complex: Basic and Clinical Issues", J. Hematology, vol. 88, suppl. 9, pp. 3-12 (May 2003).
Gorman, J. J. et al., "Studies on the Structure and Subunit Composition of Human Antihaemophilic Factor", Thrombosis Research, vol. 12, pp. 341-352 (1978).
Saundry, R. H. et al., "Chromatography of vWF on Dextran Sulphate Sepharose", Thrombosis Research, vol. 48, pp. 641-652 (1987).
Janson, J.C. et al. (editors), "Protein Purification: Principles, High Resolution Methods, and Applications", Second edition, Wiley-Liss, NY, pp. 190-191, 199-200 (1998).
Bernardi, Giorgio, "Chromatography of Proteins on Hydroxyapatite", Methods in Enzymology, vol. 27, pp. 471-479 (1973).
Barington, K. A. et al., "A Very High Purity Von Willebrand Factor Preparation Containing High Molecular Weight Multimers", Vox Sanguinis, vol. 76, pp. 85-89 (Mar. 1999).
Lethagen, S. et al., "A Comparative In Vitro Evaluation of Six Von Willebrand Factor Concentrates", Haemophilia, vol. 10, No. 3, pp. 243-249 (May 2004).
Burnouf-Radosevich, M. et al., "Chromatographic Preparation of a Therapeutic Highly Purified Von Willebrand Factor Concentrate from Human Cryoprecipitate", Vox Sanguinis, vol. 62, No. 1, pp. 1-11 (1992).
Veyradier, A. et al., "Laboratory Diagnosis of Von Willebrand Disease", vol. 28, No. 4, pp. 201-210 (Dec. 1998).
Mumby et al., Journal of Cell Biology, 1984, vol. 98: 646-652.
Labou, Journal of Chromatography B, 2003, vol. 790: 67-78.
Dumas et al., Journal of Biological Chemistry, May 28, 2004, vol. 279: 23327-23334.
Zardi et al., European Journal of Biochemistry, 1985, vol. 146: 571-579.
Schroder et al., Analytical Biochemistry, 2003, vol. 313: 1760178.
Daniel Marshak, Cold Spring Harbor Press, Strategies for Protein Purification and Characterization: A Laboratory Course Manual, 1996, p. 58.

* cited by examiner

*Primary Examiner*—Manjunath N Rao
*Assistant Examiner*—Marsha M Tsay
(74) *Attorney, Agent, or Firm*—Chalin A. Smith; Smith Patent Consulting, LLC

(57) ABSTRACT

The invention relates to a method for separating fibronectin from plasma fractions by adjusting a pH value of less than 5.4 such that fibronectin is precipitated and extracted from the solution.

14 Claims, No Drawings

PROCESS FOR REMOVING FIBRONECTIN FROM PLASMA FRACTIONS

This application is a Rule 371 U.S. National Phase Filing of PCT/EP05/009730, filed Sep. 9, 2005, which, in turn, claims priority to German Patent Application No. 10 2004 044 429.3, filed Sep. 14, 2004, the contents of which are incorporated by reference herein in their entirety.

This invention relates to a process for depleting fibronectin from plasma fractions at low ionic strength by shifting the pH to a low value so as to precipitate fibronectin and remove it from the solution.

Fibronectin consists of two polypeptide chains (α and β chains) each having a molecular weight of about 220 kDa. Its soluble form is found in the plasma and in other body fluids while its insoluble form is found in the extracellular matrix and in the underlayer or backing of membranes. The fibronectin concentrations in human plasma are 270 µg/ml on the average. On account of its affinity for cell surfaces and many different macromolecules, it has a plurality of functions, e.g. cell-cell adhesion, cell-substrate adhesion, cell division, wound healing and many more. The high affinity for surfaces and the ability of synthesizing crosslinked structures creates problems with the fractionation of human plasma into therapeutic products. Plasma fractions may form whose high fibronectin content clearly complicates filtrations, ultrafiltrations and chromatographic steps for the production of a highly pure plasma product, e.g. a concentrate of coagulation proteins. The problem often manifests itself as an early saturation or blocking of filters and chromatography columns. The enlargement, applied as a counter measure, of the filtration area or chromatography column volumes markedly increases the production cost.

Various processes for the production of isolated fibronectin fractions have been described:

Horowitz et al. (Transfusion 24, 357-362 (1984): Preparation of antihemophilic factor and fibronectin from human plasma cryoprecipitate) describe a process in which a cryoprecipitate extract serves as a starting material. Following an aluminum hydroxide precipitation, the soluble supernatant is incubated, in the model case, at 10° C. and a pH of 6.5, fibronectin precipitating and being removed by means of centrifugation. In order to produce a highly pure fibronectin preparation, the redissolved fibronectin is bound to a gelatin sepharose column and eluted at pH 5.5 by means of a sodium bromide containing buffer.

Ingham et al. (Molecular Immunology 20, 287-295 (1983): Interaction of plasma fibronectin with gelatin and complement C1q) present a study showing that fibronectin can be selectively precipitated from solutions using polyethylene glycol (PEG) 4000 in the presence of gelatin on account of specific interactions. In this connection, it turned out that at a gelatin concentration of 0.4 mg/ml, a PEG 4000 concentration of 3% suffices to precipitate 50% of the fibronectin while 11% are required for this when gelatin lacks.

European patent 0011231 B1 provides a process for the precipitation of cold-insoluble globulin (fibronectin) by the addition of 1.8-2.6 mol/l amino acids, preferably glycine, and 8-12% (w/v) neutral salt at temperatures >18° C. and separation thereof from the supernatant.

U.S. Pat. No. 4,406,886 describes a method of producing a factor VIII preparation, in which by the addition of zinc salts fibrinogen and fibronectin are precipitated in the form of zinc complexes and removed.

U.S. Pat. No. 4,278,594 provides a process for the production of a purified fibronectin fraction. Here, fibrinogen and fibronectin are precipitated in a plasma pool by means of heparin. The precipitate is dissolved, applied onto a DEAE cellulose column and fibrinogen and fibronectin are selectively eluted.

European patent EP 0503991 B1 combines two anion exchange chromatography steps with a gelatin affinity chromatography for the production of a von Willebrand factor preparation. Here, the affinity column serves above all the separation of fibronectin.

U.S. Pat. No. 5,981,254 describes a process for the production of a thrombin product, which comprises a precipitation of fibrinogen, fibronectin and factor XIII. Here, a precipitation is achieved by the addition of high salt concentrations at neutral pH values. Alternatively, this publication describes that the precipitation can be achieved by the addition of acidic salts which lower the pH. This process leads to rather high ionic strengths which have to be reduced for further process steps.

The described processes are rather time-consuming and costly, in particular when the only objective is a separation of fibronectin from the fraction of interest. Cost-intensive affinity chromatographies are often carried out. Precipitation is easier. However, it is usually obtained by the addition of polyethylene glycol or high salt concentrations, for example. The addition of precipitation reagents and high salt concentrations increase the danger that the desired product (e.g. von Willebrand factor) is partially precipitated out of the supernatant as well.

It is an object of the present invention to provide a simple process for separating fibronectin from plasma fractions so as to facilitate a further process of purifying the target protein. It has turned out surprisingly that fibronectin can be precipitated by a simple titration to a low pH value. It was particularly surprising that during stirring the fibronectin filaments formed wound around the stirrer where they formed a clot so as to be easily removed from the solution.

Therefore, the present invention relates to a process for separating fibronectin from a plasma fraction, characterized in that
(i) the pH value of the plasma fraction is adjusted to below pH 5.4 so as to form a precipitate, and
(ii) the precipitate formed is separated.

The expression "plasma fraction" refers to a composition which was obtained from plasma and contains various plasma proteins. The plasma fraction which is used as a starting composition in step (i), is a liquid composition. The liquid composition is preferably a solution or a suspension, most preferably the composition is a solution.

In a particular embodiment, the plasma fraction is dissolved cryoprecipitate. This dissolved cryoprecipitate can be previously purified by various methods. Examples thereof are aluminum hydroxide treatment, solvent/detergent treatment and/or anion exchange chromatography.

The concentration of sodium chloride or potassium chloride in the plasma fraction is preferably 50 to 250 mM, more preferably 100 to 200 mM, most preferably 120 to 150 mM.

After step (i) and before step (ii), the ionic strength of the plasma fraction is preferably below 500 mM, more preferably below 300 mM, most preferably below 200 mM. Preferably, the ionic strength is not raised strongly by adjusting the pH value in step (i), i.e. it remains preferably below 500 mM, more preferably below 300 mM, most preferably below 200 mM.

For example, the plasma fraction can contain the following buffer substances: citrate ions, acetate ions, phosphate ions and/or amino acids.

Amino acid additions are preferably used at concentrations which do not result in a protein precipitation without pH shift. With respect to glycine this means e.g. that the concentration is below 1.8 M, preferably below 500 mM, more preferably below 200 mM, most preferably below 150 mM.

The fibronectin concentration in the plasma fraction which is subjected to step (i) is usually at least 0.05 g/l, preferably at least 0.1 g/l, more preferably at least 0.25 g/l, most preferably at least 0.5 g/l. The fibronectin concentration in the plasma fraction can be e.g. 0.1 to 5 g/l, preferably 0.1 to 2 g/l.

In the process for separating fibronectin from a plasma fraction, the pH of the plasma fraction is adjusted to below pH 5.4 according to the invention. In this connection, a precipitate forms which contains fibronectin. The pH is preferably adjusted to below pH 5.3, more preferably to below pH 5.2. The adjusted pH value is thus preferably within a range of pH 4.5 to below 5.4, preferably within a range of pH 4.7 to 5.3, more preferably within a range of pH 4.8 to 5.2, even more preferably within a range of pH 4.9 to 5.1.

The pH is usually adjusted by the addition of an acidic component. Various acids can be used as the acidic component, e.g. hydrochloric acid, phosphoric acid or acetic acid.

The acidic component is usually added over a certain period of time, e.g. drop-wise. Thus, a pH within the above defined range is gradually adjusted ("titrated").

During and after the pH adjustment, the plasma fraction is preferably kept moving or mixed, e.g. by stirring. It is also preferred that after the pH adjustment the plasma fraction is further mixed for a certain period of time (e.g. by stirring), in general for at least 10 minutes, preferably for at least 20 minutes, most preferably for a period of 30 to 90 minutes. During this period, sticky aggregates form which have a considerable fibronectin content. Therefore, according to a preferred embodiment a suitable stirrer, e.g. an anchor agitator or paddle mixer, shall be used to the agitator blade of which the precipitate adheres. Thus, the precipitated fibronectin can easily be removed from the solution.

The process according to the invention can be carried out within a wide temperature spectrum, e.g. from about 1° C. to about 37° C. Preferred temperature ranges are 4 to 35° C., more preferably 10 to 30° C., most preferably the process is carried out from 20 to 25° C.

The plasma fraction used for the process according to the invention is preferably a dissolved cryoprecipitate which has been produced by processes generally known to the person skilled in the art. For example, the dissolved cryoprecipitate can be previously purified by one or more of the steps of aluminum hydroxide treatment, solvent/detergent treatment and anion exchange chromatography. The person skilled in the art is generally familiar with the conduction of these processes.

The fibronectin concentration in the plasma fraction can be reduced by at least 50% by means of the inventive process for removing fibronectin from plasma fractions. The fibronectin concentration is preferably reduced in the plasma fraction by 70 to 99%, more preferably by 80 to 99%, most preferably by 90 to 98% or by 95 to 98%.

In a particular embodiment, the loss of target protein, e.g. of VWF, is at most 50%, preferably at most 40%, more preferably at most 30%, even more preferably at most 20%, most preferably at most 10%.

Having separated the precipitate which contains fibronectin from the plasma fraction, further purification steps may follow to purify at least one coagulation factor. The coagulation factor, i.e. von Willebrand factor (VWF), is preferably further purified. In a particular embodiment, a hydroxylapatite chromatography is carried out after the pH precipitation to separate fibronectin. Hydroxylapatite is a form of calcium phosphate having the composition of $Ca_5(PO_4)_3OH$ or $Ca_{10}(PO_4)_6OH_2$, which can be used as a stationary phase for the chromatography of proteins, nucleic acids and other macromolecules. Along with the crystalline form of hydroxylapatite it is also possible to use a ceramic form which can be obtained by sintering. Hydroxylapatite can be bought from the Bio-Rad company (Munich, Germany), for example. Its ceramic hydroxylapatite is provided in two forms (type 1 and type 2). On account of larger surface areas, the type 1 material has a greater binding capacity for relatively small molecules, e.g. small proteins. In contrast, the particles of the type 2 material have larger pores which enable penetration and thus better binding of large molecules, e.g. DNA or large proteins. These materials preferably have the following properties:

TABLE 1

| | Dynamic binding capacity | Nominal pore diameter |
|---|---|---|
| Type 1 | >13.7 mg lysozyme/ml CHT* | 600-800 Å |
| Type 2 | >6.8 mg lysozyme/ml CHT* | 800-1000 Å |

*CHT = ceramic hydroxylapatite

Crystalline or ceramic hydroxylapatite is freely available. Processes for the production thereof are known in the art.

In a first variant, the hydroxylapatite chromatography comprises that (i) the plasma fraction is contacted with a hydroxylapatite matrix after the separation of the precipitated fibronectin precipitate so as to bind fibrinogen and/or fibronectin to the hydroxylapatite matrix while VWF is not substantially bound to the hydroxylapatite matrix, and optionally thereafter (ii) unbound von Willebrand factor (VWF) is separated from the hydroxylapatite matrix. This variant is referred to as "flow chromatography" in the present application since VWF does not bind to the hydroxylapatite matrix. The process can be carried out as a column chromatography or batch process; it is preferred to carry it out as a column chromatography. In the case of column chromatography, VWF is in the flow and at least one contaminating protein, e.g. fibronectin and/or fibrinogen, is bound to hydroxylapatite.

According to this first variant, the hydroxylapatite chromatography is carried out at a pH of 6.5 to 8.5, preferably 6.8 to 8.5, more preferably 6.8 to 7.5, most preferably 7.0 to 7.5. Running, wash and elution buffers as well as the protein solution to be applied usually have the same pH value. However, variants where these solutions have different pH values are also practicable. The composition which is contacted with the hydroxylapatite matrix preferably contains sodium phosphate and/or potassium phosphate. The total concentration of sodium phosphate and/or potassium phosphate in the solution is e.g. 0 to 100 mM, preferably 10 to 50 mM, most preferably 20 to 40 mM, i.e. a buffer solution having said concentrations can be used as a running buffer. The composition is applied onto a hydroxylapatite column at a low salt concentration of 0-100 mM, preferably 10-50 mM, potassium or sodium phosphate at a pH of preferably 6.8 to 8.5, more preferably at a pH of 7.0-7.5. In this variant, the hydroxylapatite is preferably ceramic hydroxylapatite, more preferably of type 1, as sold by Bio-Rad (Munich, Germany). Under these conditions, the majority of VWF molecules do not bind to the matrix and are in the flow while the majority of contaminating proteins, such as fibrinogen or fibronectin, bind to the matrix.

By means of flow chromatography it is possible to obtain preparations which only contain small amounts of fibrinogen and fibronectin. The fibrinogen antigen concentration in the flow fraction is usually below 25 μg/ml, preferably below 15 μg/ml, more preferably below 10 μg/ml, most preferably at most 5 μg/ml. The concentration of fibronectin antigen in the flow fraction is usually below 250 µg/ml, preferably below 150 µg/ml, more preferably below 100 µg/ml, most preferably at most 50 µg/ml. The concentration of fibrinogen antigen and fibronectin antigen can be determined by generally known processes, e.g. as described in the examples of the present application.

The fibrinogen concentration in the flow fraction is preferably below 10%, more preferably below 5%, even more preferably below 2.5% of the fibrinogen concentration in the loading solution (prior to flow chromatography). The fibronectin concentration in the flow fraction is preferably below 10%, more preferably below 5%, even more preferably below 2.5% of the fibronectin concentration in the loading solution (prior to flow chromatography). Flow chromatography is particularly suited to purify VWF. Thus, the VWF yield of flow chromatography (based on the mass balance) is usually above 50%, preferably above 60%, most preferably above 75%. The specific activity (ristocetin cofactor activity per mg total protein) can be raised by flow chromatography by at least 100%, preferably by at least 150%, most preferably by at least 200%.

A second variant of the hydroxylapatite chromatography is particularly favorable for a purification of VWF. In this second variant, VWF is bound to the hydroxylapatite matrix and then eluted. This variant is referred to as "binding chromatography" in the present application. The binding chromatography usually comprises that
(a) VWF is bound to the hydroxylapatite matrix,
(b) contaminations are washed out at a lower salt concentration, and
(c) the VWF containing fraction of interest is subsequently eluted at a higher salt concentration.

In step (a), a solution containing VWF and one or more contaminating proteins is contacted with the hydroxylapatite matrix. The total concentration of sodium and/or potassium phosphate in this solution is usually 0 to 200 mM, preferably 1 to 200 mM, more preferably 1 to 50 mM, most preferably 10 to 30 mM.

In wash step (<b), the hydroxylapatite matrix is washed with a buffer having a low salt concentration. The total concentration of sodium and/or potassium phosphate in this wash buffer is usually 100 to 300 mM, preferably 150 to 250 mM, most preferably 180 to 240 mM.

In step (c), the VWF containing fraction of interest can be eluted with a buffer having a higher salt concentration. The elution buffer usually contains 200 to 500 mM, preferably 250 to 400 mM sodium and/or potassium phosphate.

Yield and purity can be changed by changing the salt concentrations. The higher the salt concentration in the wash buffer, the cleaner the resulting fraction of interest. However, the yield is lowered by this. Furthermore, the selected pH value influences the optimum salt concentration for the wash buffer. The lower the pH, the stronger the binding of VWF to the hydroxylapatite matrix. Correspondingly, the selected salt concentrations can be higher with lower pH values and lower with higher pH values. The (binding) hydroxylapatite chromatography is carried out at a pH of 5 to 7.5, preferably 5.5 to below 6.8, most preferably 6.0 to 6.5. Running, wash and elution buffers and the protein solution to be applied usually have the same pH. However, variants where these solutions have different pH values are also practicable.

In this second variant, the VWF containing solution, e.g. the plasma fraction after pH precipitation and separation of the fibronectin precipitate, is applied onto a hydroxylapatite column, e.g. ceramic type 2 hydroxylapatite, at a low salt concentration, preferably 0-100 mM, more preferably 10-30 mM, potassium or sodium phosphate at a pH of 5.5-6.8, preferably 6.0-6.5. The majority of the VWF molecules are bound under these conditions. Contaminations, e.g. fibronectin, can be washed out by washing with a solution at a higher salt concentration using e.g. potassium or sodium phosphate, e.g. 230 mM sodium phosphate, pH 6.0. The fraction of interest is then eluted with highly concentrated salt solutions, e.g. phosphate solutions, such as 400 mM sodium phosphate, pH 6.0, for example.

VWF preparations which are virtually free from detectable amounts of fibrinogen and fibronectin can be obtained by binding chromatography. If the loading solution which is contacted with the hydroxylapatite matrix is a plasma fraction and/or contains fibrinogen or fibronectin, it is possible to obtain a virtually quantitative removal of the contaminating proteins, i.e. fibrinogen and fibronectin, from the solution. Thus the fibrinogen concentration in the elution fraction is preferably lower than 25% of the fibrinogen concentration in the loading solution (before the binding chromatography). The fibronectin concentration in the elution fraction is preferably lower than 10%, more preferably lower than 5%, of the fibronectin concentration in the loading solution (before the binding chromatography). The concentrations of fibrinogen and/or fibronectin in the elution fraction (fraction of interest) are usually below the detection limit of about 1 µg/ml.

VWF preparations having a high specific activity can be obtained by binding hydroxylapatite chromatography. The specific activity in the elution fraction can be above 50 U/mg protein, preferably it is above 75 U/mg protein, more preferably above 85 U/mg protein, most preferably at least 100 U/mg protein. The VWF activity is determined by the ristocetin cofactor assay which determines the binding capacity of VWF to the platelet receptor glycoprotein Ib/IX under the influence of the ristocetin antibiotic. The specific VWF activity can be determined as described in the examples.

For the production of a particularly pure VWF preparation it is possible to combine the two described variants of hydroxylapatite chromatography with each other or with other purification methods. As has turned out, it is particularly useful to initially carry out flow chromatography with hydroxylapatite according to the above described process to deplete the main contaminations. Then, the fraction of interest is titrated to pH 6.0 with 1 M HCl, for example. As described for binding chromatography, the sample is applied onto a hydroxylapatite column. VWF molecules are bound and eluted selectively. VWF molecules are bound and eluted selectively. In a third variant of hydroxylapatite chromatography, flow chromatography with hydroxylapatite is initially carried out, VWF not binding to the hydroxylapatite matrix, and then the flow fraction is re-chromatographed under binding conditions and the VWF fraction is eluted. In connection with flow chromatography it is useful, but not necessary, to use phosphate ions as a buffer substance. Phosphate is a specific agent for the elution of VWF in the binding chromatography.

The embodiments described in this application can be combined.

Solutions which can be freed from fibronectin by the process described herein are plasma fractions from which other components shall be purified. They may be plasma fractions from which e.g. coagulation preparations, such as the von Willebrand factor, are isolated. The plasma fractions which can be recovered by means of this process, contain, as a main contamination, fibronectin which is present in concentrations of >0.1 g/l. By the addition of an acidic component, e.g. 1 M hydrochloric acid, the solution is titrated to a pH<5.4, preferably 5.4 to 4.8, more preferably 5.2 to 5.0. The solution is incubated >10 minutes, preferably for 30 to 90 minutes, with stirring. Sticky aggregates form which when a suitable stirrer is used, e.g. an anchor agitator or paddle mixer, stick to the agitator blade and are removed from the solution in this way. The advantage of this is that a majority of the precipitate does not have to be removed in a technically time-consuming and cost-intensive way by means of filtration or centrifugation. The effectiveness of the filament formation is influenced by the ionic strength. Very good results were obtained with buffer solutions, for example, which contained 100-200 mM NaCl, preferably 120-150 mM NaCl. The process can be carried out within a wide temperature spectrum of e.g. 4° C. to 35° C. The process is preferably carried out at room temperature. The depletion effectiveness for fibronectin depends on the composition of the solution and is typically between 70% and 95%.

The below examples explain the invention in more detail.

EXAMPLE 1

Precipitation of Fibronectin on a Laboratory Scale at Various Temperatures

As a starting material, a cryoprecipitate solution was used which was previously purified by aluminum hydroxide precipitation, Polysorbate 80/TNBP treatment and anion exchange chromatography, as described in WO 9315105 A1, for example. First, disturbing fibronectin had to be removed to isolate the resulting von Willebrand factor (VWF). As main components, the solution contained 0.18 g/l VWF antigen (VWF-Ag), 0.05 g/l fibrinogen antigen, and 1.49 g/l fibronectin antigen. The solution contained the following buffer substances: 10 mM citrate, 160 mM NaCl, 120 mM glycine, 1 mM $CaCl_2$. 1 l of the solution at a time was titrated to pH 5.2 by the addition of 1 M HCl at 4° C., 20° C. and 35° C. with stirring. During incubation for 60 min, white fibronectin filaments wound around the stirrer in all 3 cases and formed a massive clot. It was possible to easily clear-filtrate the remaining solution using a membrane filter.

TABLE 2

Composition of the starting sample and of the precipitated 4° C., 20° C. and 35° C. samples

|  | VWF-Ag [g/l] | Fibrinogen-Ag [g/l] | Fibronectin-Ag [g/l] |
|---|---|---|---|
| Stock | 0.18 | 0.05 | 1.49 |
| 4° C. | 0.14 | 0.01 | 0.09 |
| 20° C. | 0.15 | 0.02 | 0.04 |
| 35° C. | 0.16 | 0.02 | 0.1 |

It has turned out that within the temperature range of 4° C. to 35° C. a pH shift precipitation is excellently suited to separate large amounts of fibronectin. The maximum loss of target protein VWF is here 22% (4° C.) with a fibronectin depletion of at least 93% to 97%.

The WVF antigen concentration was determined by means of the STA® Compact of Diagnostic Stago company (Roche Diagnostics, Mannheim, Germany) and its test reagents (STA LIA vWF).

In order to determine the amount of fibrinogen antigen and fibronectin antigen, nephelometric methods were used for the quantitative determination of the fibrinogen antigen and fibrinogen antigen concentration in the Beckman-Arrays 360 (Beckman Coulter, Monheim, Germany).

EXAMPLE 2

Separation of Fibronectin in a Preparative Batch

A protein solution was used which was previously purified as in Example 1 and was present in the same buffer system. 40 l of this solution were titrated to pH 5.2 at room temperature and incubated with stirring for 60 min. Fibronectin aggregates were largely removed from the solution by adhering to the agitator blade of the stirrer. Following clear-filtration via a membrane filter, the solution could be further processed to obtain a VWF preparation.

TABLE 3

Precipitation of fibronectin in a preparative 40 l batch

|  | VWF-Ag [g/l] | Fibrinogen-Ag [g/l] | Fibronectin-Ag [g/l] |
|---|---|---|---|
| Stock | 0.20 | 0.07 | 1.33 |
| After titration and filtration | 0.19 | 0.03 | 0.13 |

90% of fibronectin could be removed with a loss of only 5% of target protein VWF.

ADDITIONAL CITATIONS

The following citations are mentioned additionally in connection with various analytical methods.

VWF Activity:
Veyradier A, Fressinaud E, Meyer D (1998): Laboratory diagnosis of von Willebrand disease. Int J Lab Res 28 (4): 201-210.

VWF Antigen:
Budde U, et al. (1984): Acquired von Willebrand's disease in the myeloproliferative syndrome. Blood 64 (5): 981-985.
Newman D J, Henneberry H, Price CP (1992): Particle enhanced light scattering immunoassay. Ann Clin Biochem 29 (Pt1): 2242.

Fibronectin Antigen:
Sandberg L, et al. (1985): Plasma fibronectin levels in acute and recovering malnourished children. Clin Physiol. Biochem. 3(5):257-264.
Colli A, et al. (1986): Diagnostic accuracy of fibronectin in the differential diagnosis of ascites. Cancer: 58(11):2489-2493.

Fibrinogen Antigen:
Ernst E, Resch K L (1993): Fibrinogen as a cardiovascular risk factor: a meta-analysis and review of the literature. Ann Intern Med.: 118(12):956-963.
Jelic-lvanovic Z, Pevcevic N (1990): Fibrinogen determination by five methods in patients receiving streptokinase therapy. Clin Chem.: 36(4):698-699.

The invention claimed is:
1. A process for the production of a composition containing at least one coagulation factor, said process consisting of the following steps:
i. adjusting the pH of a plasma fraction, wherein said plasma fraction contains an initial amount of fibronectin and at least one coagulation factor, contains NaCl or KCl at a concentration of 100-200 mM and is characterized by an ionic strength below 500 mM, to a value between pH 4.7 and pH 5.3 so as to form a precipitate comprising 70% to 99% of the initial amount of fibronectin and a supernatant containing said at least one coagulation factor, ii. removing the fibronectin precipitate formed in step (i) to thereby yield a composition containing at least one coagulation factor; and iii. purifying the at least one coagulation factor from the composition obtained in step (ii), wherein steps (i) and (ii) are performed at a temperature that ranges from 20° C. to 25° C.

2. The process according to claim 1, characterized in that the ionic strength of the plasma fraction is below 300 mM.

3. The process according to claim 1, characterized in that the ionic strength of the plasma fraction is below 200 mM.

4. The process according to claim 1, wherein removing step (ii) consists of stirring the plasma fraction for at least 10 minutes.

5. The process according to claim 1, characterized in that the majority of the fibronectin precipitate is separated by means of an agitator blade of a stirrer.

6. The process according to claim 1, characterized in that the plasma fraction initially contains fibronectin at a concentration of at least 0.1 g per liter.

7. The process according to claim 1, characterized in that the plasma fraction initially contains glycine at a concentration below 500 mM.

8. The process according to claim 1, characterized in that the plasma fraction initially contains glycine at a concentration below 200 mM.

9. The process according to claim 1, characterized in that the plasma fraction initially contains glycine at a concentration of 50 to 200 mM.

10. The process according to claim 1, characterized in that the plasma fraction initially contains glycine at a concentration of 100 to 150 mM.

11. The process according to claim 1, characterized in that the plasma fraction is dissolved cryoprecipitate.

12. The process according to claim 11, characterized in that the dissolved cryoprecipitate is previously purified by (a) treatment with aluminum hydroxide, (b) treatment with a solvent and/or a detergent, and (c) anion exchange chromatography.

13. The process according to claim 1, characterized in that the at least one coagulation factor is von Willebrand factor.

14. The process according to claim 1, wherein the fibronectin precipitate obtained in step (i) contains at least 90% of the initial amount of fibronectin.

* * * * *